(12) United States Patent
Sullivan

(10) Patent No.: US 7,319,039 B2
(45) Date of Patent: Jan. 15, 2008

(54) AEROSOL-BASED DETECTION OF BIOLOGICAL AGENTS

(75) Inventor: Brian M. Sullivan, Manhattan Beach, CA (US)

(73) Assignee: Northrop Grumman Corporation, Los Angeles, CA (US)

( * ) Notice: Subject to any disclaimer, the term of this patent is extended or adjusted under 35 U.S.C. 154(b) by 470 days.

(21) Appl. No.: 10/985,602

(22) Filed: Nov. 9, 2004

(65) Prior Publication Data

US 2006/0262318 A1    Nov. 23, 2006

(51) Int. Cl.
    *G01N 21/76*    (2006.01)
(52) U.S. Cl. .................. 436/172; 356/318; 250/458.1; 436/181
(58) Field of Classification Search ................ 422/83, 422/82.05–82.09; 356/335–343, 437; 436/172; 250/458.1–461.2
    See application file for complete search history.

(56) References Cited

U.S. PATENT DOCUMENTS

| | | | | |
|---|---|---|---|---|
| 4,651,010 A * | 3/1987 | Javan | ...................... | 250/458.1 |
| 6,066,295 A * | 5/2000 | Bernstein et al. | .............. | 422/50 |
| 6,194,731 B1 * | 2/2001 | Jeys et al. | ................ | 250/461.2 |
| 6,593,582 B2 * | 7/2003 | Lee et al. | ................. | 250/458.1 |
| 6,607,889 B1 * | 8/2003 | Coull et al. | ..................... | 435/6 |
| 6,608,677 B1 * | 8/2003 | Ray et al. | .................... | 356/301 |
| 6,831,279 B2 * | 12/2004 | Ho | .......................... | 250/458.1 |
| 7,073,748 B2 * | 7/2006 | Maurer et al. | .............. | 244/1 R |
| 2003/0098421 A1 * | 5/2003 | Ho | .......................... | 250/458.1 |
| 2004/0259226 A1 * | 12/2004 | Robey et al. | ............ | 435/252.3 |
| 2005/0200481 A1 * | 9/2005 | Wallach | ....................... | 340/541 |
| 2005/0214168 A1 * | 9/2005 | Lin et al. | ...................... | 422/83 |

OTHER PUBLICATIONS

Li, Jianwei J., "Molecular Aptamer Beacons for Real-Time Protein Recognition", Biochemical and Biophysical Research Communications vol. 292 (2002), pp. 31-40.*
Smith, Drew, "Sensitivity and Specificity of Photoaptamer Probes", Molecular and Cellular Proteomics vol. 2.1 (2003) pp. 11-18.*

* cited by examiner

*Primary Examiner*—Tarifur Chowdhury
*Assistant Examiner*—Jonathan M Hansen
(74) *Attorney, Agent, or Firm*—Ronald M. Goldman; Connie Thousand

(57) ABSTRACT

The presence of an aerosol or cloud (3) of a toxic substance is detected by producing an aerosol (17, 5) of ligands (13) to the target substance in a region of sky that contains the target substance, permitting molecules the target substance to bind to the ligand, directing light (7, 21) of a first frequency into the revised aerosol; and then inspecting (9, 25) the revised aerosol for emissions of light of a second frequency. When light of the second frequency exists an alarm (15, 31) is initiated.

7 Claims, 1 Drawing Sheet

- 17 PRODUCE AEROSOL IN SUSPECT REGION
- 19 DELAY 1
- 21 TRANSMIT COHERENT BEAM OF LIGHT INTO SUSPECT REGION AT FREQUENCY F1
- 23 DELAY 2
- 25 ANALYZE LIGHT EMISSIONS FROM REGION TO DETECT LIGHT OF F2
- 27 IS F2?
- 31 YES — SOUND ALARM
- 29 NO — END

AEROSOL-BASED DETECTION OF BIOLOGICAL AGENTS

FIELD OF THE INVENTION

This invention relates to biological warfare defense systems. More particularly, the invention relates to an aerosol based method of detecting dispersed airborne biological agents in sufficient time to avoid contamination of and give an effective warning to the intended target.

BACKGROUND

A technique for delivering harmful biological agents to enemy battlefield combatants is in an aerosol. The microscopic agent particles are usually dry, but could be carried in a compatible liquid. That material is sprayed or otherwise released into the atmosphere as an aerosol by an exploding shell, a missile or an aircraft in the general vicinity of the targeted combatants. Depending on the prevailing winds, the aerosol or cloud, as variously termed, may be released some distance from the target combatants and the prevailing wind is allowed to carry the cloud to the location where the combatants may be exposed.

In one dictionary definition, the term cloud is defined as a visible mass of minute particles suspended in the air or in a gas. The term aerosol is defined as a suspension of fine solid or liquid particles in gas. Smoke, fog, and mist are given examples of an aerosol. Significant overlap is apparent. Aerosol also refers to the manner in which the particles were dispensed into the air, i.e. a substance dispensed from a pressurized container as an aerosol.

As becomes clear from study, agent particles may be so small and the density very light so that the mass of those suspended particles need not be visible to the naked eye. As one also understands, the particles may be small and heavier than air, and yet may be suspended in the air, even though individually the particles are heavier-than-air. Even though suspended in air, if the ambient air remains still, the particles may settle out of suspension and deposit on surfaces, remaining just as deadly. The toxin Anthrax is an example of the latter. It should thus be understood, that all those possibilities are encompassed within either of the terms aerosol or cloud as used in this application, whether the particles are visible to the eye or not, and the terms subsume such extensions of the dictionary definitions.

Currently, there is no good method known for remotely and directly detecting the presence of aerosolized biological agents. Toxins are particularly troublesome because they are fast-acting and disabling. Some of the more notorious toxins include botulism toxin, staphylococcal enterotoxin B, and ricin. By the time sensors of existing design are able to produce an alarm, personnel are already sick, in the throes of dying or already dead. The picture is not pretty.

Some might urge that detection of agent aerosols lacks utility, since that form of warfare has been outlawed by treaty and all world organizations. Notwithstanding, not all nations subscribe to those treaties and, of course, treaties have at times been broken or rationalized by renegade nations. The problem remains. Hence, there remains utility in detecting airborne agents. The result is that the prudent nation should develop defensive measures. Detection techniques are an appropriate part of those measures. And that's only the military picture, where one nation wishes to destroy clusters of troops of another nation on the battlefield.

A mentally deranged person who possesses a can of aerosol filled with a biotoxin may be able to rent and pilot a small plane to spray the aerosol over New York City, as example, a favorite symbolic spot. It's easy to obtain the small plane, and even to rent a pilot. Obtaining the biotoxin is not so simple, yet not impossible. And the targeted victims or their protectors the police and the military cannot detect the oncoming cloud of antigens in a timely manner. At best, they might rely on the Biowatch system, which currently provides warning in days, not minutes or hours.

Accordingly, an object of the invention is to provide warning of a toxin laden cloud.

A further object of the invention is to detect toxin laden clouds in sufficient time to allow targeted persons to take protective measures to avoid or defeat the toxicity.

SUMMARY OF THE INVENTION

In accordance with the method, rapid, sensitive, and selective daytime Biological Warfare ("BWA") cloud identification is accomplished by the release of taggants, distinctive photoaptamers that recognize (e.g. are able to attach to) specific bioagent proteins into the atmosphere in the region of the suspect BWA cloud, subsequent binding of the taggant selectively with the bioagent (or bioagents) of interest, when present, and detection of the binding by means of a UV-laser-triggered fluorescence process.

Tagged or untagged, aptamers and photoaptamers are created to naturally attach to specific molecules and serve in effect to recognize that specific molecule. Hence, photoaptamers (and aptamers as well) are sometimes referred to as recognition molecules. In one approach to the latter process two fluorescent-tagged recognition molecules of a complementary kind are delivered to and mixed with the suspect toxin-containing aerosol as small liquid droplets and then are exposed to light of a particular frequency. Exposed to that light, the tags undergo fluorescence resonance energy transfer (FRET) when one of each kind of taggant is bound to respective positions on the same molecule of the target toxin and are thereby tethered to the molecule only about ten to one hundred angstroms apart. The distance dependence of FRET is expected to result in low rates of false alarms.

As an advantage, the recognition molecules are photoaptamers that, through their photo-cross-linking capability, enable higher specificity than "regular" aptamers, while providing significant durability as compared to antibodies. Through directed evolution by means of the Photo-SELEX process, photoaptamers can be selected to perform more reliably in the aerosol phase than antibodies. In a specific embodiment, the liquid droplets will be composed of ethylene glycol, selected for its low vapor pressure over a wide range of temperatures, its compatibility with aqueous biochemistry, its relative safety and its low price.

In accordance with the method, an aerosol containing approximately equal quantities of two fluorophore tagged photoaptamers to a target agent, such as a suspect protein or bacteria, is released into a cloud (or region of the air) that one believes to contain targeted agents. If the cloud contains a targeted agent, the two distinct photoaptamers, one of whose attached fluorophore is regarded as a energy donor and the other of whose attached fluorophore is regarded as an energy acceptor, bind to different locations on the molecule of the suspect bioagent, molecular locations that are sufficiently close in proximity to permit fluorescent resonance energy transfer from the donor photoaptamer to an acceptor photoaptamer to occur under the appropriate circumstances.

The foregoing and additional objects and advantages of the invention, together with the structure characteristic thereof, which were only briefly summarized in the foregoing passages, will become more apparent to those skilled in the art upon reading the detailed description of a preferred embodiment of the invention, which follows in this specification, taken together with the illustrations thereof presented in the accompanying drawings.

BRIEF DESCRIPTION OF THE DRAWINGS

In the drawings:

FIG. 1 is a pictorial showing one form of equipment for carrying out the new method; and FIG. 2 is a block diagram of the steps of one embodiment of the new method.

DESCRIPTION OF THE PREFERRED EMBODIMENTS

The pictorial of FIG. 1 illustrates the interaction between an unmanned airborne vehicle ("UAV") 1 and a cloud 3 of an aerosolized bioagent, such as Anthrax, located at some distance, say five to ten km, from a group of military personnel, not illustrated, who are the intended target for the toxic cloud. The UAV is a radio-controlled unmanned aircraft, such as the much publicized "Predator" aircraft manufactured by the General Atomics company, that was additionally fitted with a radio-controlled ("RC") sprayer 5, depicted on the underside of the UAV, an RC controlled laser 7 and an RC computer-controlled spectrometer 9. The UAV and the on-board equipment is controlled by the military personnel from a ground station 11. Such aircraft typically also include a television camera and associated TV transmitter, not illustrated, to broadcast television pictures to that ground station, and a global positioning system receiver ("GPS" receiver) and transmitter to broadcast position information of the aircraft to station 11 and give the craft's position to the controllers.

Sprayer 5, pictorially illustrated, may be any industrial type sprayer suitable for spraying from an aircraft, as example the crop-dusting sprayers that dispense liquid fertilizers onto crops. The sprayer on board a UAV (or UGV or an exploding howitzer shell for that matter) is able to deliver fine liquid droplets. Once delivered into the suspect cloud, some mixing time is required for the liquid droplets to mix with any bio-aerosols in the suspect cloud.

As shown in the figure, the fully equipped UAV is sent into the sky and flown to the region containing the cloud 3 that is to be investigated for the suspect bioagent. Any such cloud 3 is basically in the form of microscopic size particles that define a mist or fog like structure. If the cloud is indeed toxic, the toxicity would have been man-made and the mist would have been released at some region of the sky, from where it was intended to drift under motivation of the prevailing winds in the direction of the targeted combatants. For that to occur, the source would have dispensed the aerosol from a pressurized container or other sprayer, much like the sprayer 5 that is contained in the UAV. Alternatively, the bioagent could have been released from an artillery shell that explodes and disperses the bioagent cloud.

In this first embodiment, when the presence of a suspect cloud is first noted, the defenders must decide on the particular bioagent(s) that might be present in the cloud, if the enemy being defended against is one who is suspected of having bioagent application capability. The educated guess may be based on intelligence information, rumors and heresay that existed prior to the initiation of the conflict or even more current information. In preparation, sprayer 5 is loaded with a photoaptamer, a tagged photoaptamer that attaches or binds to the suspect bioagent at the molecular level in a liquid that is neutral relative to the photoaptamer, as example, ethylene glycol.

"Aptamers" are oligonucleotides selected for specific binding to a variety of molecular targets, ranging from small organics to proteins. These nucleic acid-binding species can consist of RNA, DNA, or modified nucleotides and are typically 15 to 60 nucleotides long. Their binding affinities range from Kd's of 1 pM to 1 µM, with most in the 1-10 nM interval. A "photoaptamer" is an aptamer that has BrdU ("Bromo-deoxy-Uridine") instead of T ("Thymine"). BrdU can form a covelent bond with a target upon excitation by ultraviolet light of a particular wavelength. T cannot. Aptamers (and photoaptamers) are selected using a relatively rapid in vitro selection process (the SELEX process later described) and can be inexpensively synthesized. Aptamers (and photoaptamers) can be engineered using standard nucleic acid techniques to incorporate radioisotope, fluorescent, or other reporters. If fluorescent, the fluorescent dye that is attached or labeled to the aptamer is referred to herein as the "fluorophore" and the reporter is thus an optical one. Fluorophores, molecules that absorb light at a particular wavelength and emit at a different wavelength, can be covalently attached to either aptamers or photoaptamers to generate fluorophore-labeled versions of the molecules. Not only can "labeled" aptamers and photoaptamers, mimic antibodies in detecting protein targets, they also serve as reagents that directly transduce molecular recognition into optical signals. See also Hamaguchi et al, Hamaguchi, Ellington & Stanton, "Aptamer Beacons for the Direct Detection of Proteins," *Analytical Biochemistry*, 294, 126-131 (2001).

As noted in an article by Drenckhahn, D., and T. D. Pollard (1986), "Elongation of Actin Filaments is a Diffusion-Limited Reaction at the Barbed End and Is Accelerated by Inert Macromolecules," Journal of Biological Chemistry, 261 (Sept. 25):12754-12758, water and ethylene glycol are interchangeable as solvents in biochemical reaction systems. The only difference is that reactions proceed more slowly in ethylene glycol because of its increased viscosity. The recognition biochemistry should be hosted by a liquid solvent system, and the solvent system must be compatible with aqueous biochemistry, but not materially interfere with the transmission of light. The solvent system should also have low vapor pressure over a wide range of temperatures so the system can be used without evaporation in hot, dry climates. Ideally, the system should also be relatively nontoxic. Ethylene glycol satisfies all of the requirements and, as an added bonus, the substance is inexpensive as a result of its large scale manufacture as a component of automotive antifreeze. Ethylene glycol thus appears to be the preferred solvent for a practical embodiment of the present invention.

Remotely controlled by station 11, UAV 1 takes off in flight and intercepts cloud 3. As the UAV progresses through the cloud, on command from ground station 11 sprayer 5 dispenses a cloud or fog 13 in the same region as cloud 3. If desired, the UAV may make multiple dispensing passes through the cloud. The substance of cloud 13 mixes and interacts with the substance of cloud 3 to form a super cloud or, as variously termed, a revised cloud.

As later herein more fully discussed, on release, the microscopic droplets containing the photoaptamer possess some kinetic energy. Further, some percentage of those droplets connect with corresponding droplets of the target bioagent in cloud 3. When that occurs the photoaptamer and the agent droplets coalesce. The foregoing action is much the same action that occurs when a rain cloud is seeded with Iodide to produce man-made rain.

The UAV is then guided out of the cloud and flown around to a point where a "look-back" observation of the revised cloud can be made, ideally guided by personnel at station 11 with the assistance of the television camera in the UAV and/or that of the GPS system. Laser 7, represented by the aiming sight symbol on UAV 1, is directed into the revised cloud. In this embodiment laser 7 is a diode-pumped Nd:YAG ("YAG") laser system that serves as the light source for the detection system and preferably is reliable, small in size, and light in weight. For greater versatility in other embodiments, later discussed, the laser may be tunable, specifically, a tunable ultraviolet laser UV laser (TUV). UV lasers are suitable for the excitation of a europium-type donor and for cross-linking photo-aptamers. The laser emits light of a frequency (e.g. color) that is the frequency at which a fluorophore linked to the photoaptamer contained in sprayer 5 accepts, that is, inputs energy (i.e. acceptor frequency). By the movement of the UAV, the light emitted by the laser covers a significant portion of the revised cloud, and, hence, is incident on the photoaptamer linked bioagent molecules of the suspect bioagent, if the suspect bioagent was present, or on the unlinked photoaptamers if no such suspect bioagent was present.

Assuming the suspect bioagent is present, a short time following energization by the laser, the fluorophore linked to the photoaptamer or, as fluorophore-photoaptamer conjugate, as variously termed, emits light (e.g. photons) of the emission frequency of the linked fluorophore. The foregoing luminance action is known as resonance emission of Fluorescence Resonance Energy Transfer, earlier briefly mentioned and discussed latter herein in greater detail. That emission is detected by the spectrometer 9 carried in the UAV and that information is relayed in turn by radio to ground station 11, which sounds an alarm 15 at that station. Knowing that the bioagent is around, defensive measures can be taken to protect personnel. One defensive measure is for the military personnel to take cover in an air tight bunker or tent. Another is to takes steps to neutralize the bioagent in the cloud, the procedure for which is outside the scope of the present invention and need not be discussed.

An alternative platform for delivering detection cloud 13 to the region is a field artillery piece, such as a howitzer with a range of twenty-three miles, because of the available range, speed and relatively low cost. The artillery shell containing the detection photoaptamers is loaded into the howitzer, the aim to the target adjusted, and the artillery piece is fired, sending the shell on its way. The shell is fused so that it is timed to explode on reaching the desired height and distance, placing the shell in the suspect region of the sky. More preferred platforms are the newly developed unmanned aerial vehicle (UAV), earlier described, and the unmanned ground vehicle (UGV). Both unmanned platforms are able to access areas too dangerous or inaccessible for manned platforms. The UAV is preferred over the Howitzer because of greater versatility, and the ability to both provide cloud delivery and house a detector. Additionally, a UAV can fly over a much longer distance, well beyond 50 km, to interrogate a potential threat cloud. The UGV possesses similar capabilities as a UAV, being able to both deploy and detect. A UGV provides further advantage as a detection platform of being able to look up through the cloud with sky background as a backdrop, which is advantageous, as opposed to looking down on the more cluttered ground background. It is believed that the ability to look up through the cloud appears to enable daytime detection. However, for convenience of delivery into the suspect cloud the UAV was used in the embodiment of FIG. 1.

The foregoing detection procedure of FIG. 1 is presented in more general terms as a block diagram in FIG. 2 to which reference is next made. The first step 17 is to produce an aerosol in the same region of the sky that contains the suspect bioagent, as by spraying or releasing the aerosol so that the aerosol moves into contact and merges with the cloud of suspect bioagent. That aerosol is constituted of a photoaptamer that is capable of linking to the suspect bioagent in a liquid base, such as ethylene glycol. It is believed that the kinetic energy of the droplets of the released aerosol cause sufficient movement and have sufficient momentum to strike and merge with corresponding droplet of the suspect cloud, allowing the photoaptamer to come into the vicinity of a particle of the suspect bioagent, and, ultimately, to interlock, attach or link as variously termed. The merger is not entirely accomplished, but a useful measurable quantity of such mergers occurs in a short time. For purpose of this description, it is assumed that the suspect bioagent is in fact present in the original cloud. The result produced in the foregoing merger are photoaptamer linked agents.

As represented by the delay 19, following the delay period, as example, one minute, a laser light source is pointed into the revised cloud and fired to produce a beam of coherent light in the suspect cloud. By design, the laser is one that has an output frequency, i.e. color, that is the same as the excitation frequency of the fluorophore of the photoaptamer. The coherent light strikes many of the photoaptamers in the revised cloud. Each photoaptamer receiving that light-energy excitation reacts in one of two ways, depending on the kind of fluorophore pair that was used.

The first kind is the fluorophore pair, one fluorophore being a donor of energy and the other one being an emitter of light energy, also known as an "acceptor". The separate aptamers to which each of the fluorophores attach are by design known to both attach to a molecule of the suspect bioagent at molecular locations in which the two fluorophores are physically spaced about 10-50 angstroms from each other. Because the two fluorophores are so close to one another, the two fluorophores will exhibit the property of fluorescence resonance energy transfer, a physical phenomenon known to scientists.

Fluorescence Resonance Energy Transfer or FRET is a physical process in which an excited fluorescent donor dye transfers its energy to a nearby acceptor dye without emitting a photon. The dye is excited by exposing the dye to light of the frequency (e.g. color) which the dye absorbs, boosting the energy level of the dye. The phenomenon has strong, sixth-power, distance dependence and is 50% efficient when the dyes are on the order of tens of angstroms (50 angstroms is common) apart. The interfluorophore distance corresponding to 50% FRET efficiency is termed the "Forster radius." FRET enables a system in which free acceptor and donor dye molecules in solution do not produce an appreciable FRET signal due to the small likelihood of their coming sufficiently close to each other. They only produce a signal when they are tethered to the same molecule, tens of angstroms apart. See Van Der Meer, B. W., G. Coker III, S.-Y. Simon Chen, "Resonance Energy Transfer: Theory and Data," VCH Publishers, Inc., New York, 1994. The interaction between the electronic excited states of two dye molecules in which excitation by FRET is transferred from a donor molecule to an acceptor molecule is distance-dependent. The donor and acceptor molecules must be in close proximity, typically 10-100 Å. Furthermore excitation spectrum of the emitter must overlap the fluorescence emission spectrum of the donor.

The second kind of photoaptamer pair is referred to herein as the conjugate pair of donor-quencher fluorophores and is described as a "molecular beacon" in an article by Hamaguchi et al, Hamaguchi, Ellington & Stanton, "Aptamer, Beacons for the Direct Detection of Proteins," *Analytical Biochemistry*, 294, 126-131 (2001) Aptamer molecular beacons can adopt two or more conformations, one of which allows ligand binding. A fluorescence-quenching pair of fluorophores is used to report changes in conformation induced by ligand binding. As stated in the article: "Molecular beacons are designed to form a stem-loop structure with a fluorophore on one end of the stem and a quencher on the other end. The fluorophore is quenched by energy transfer to the quencher in close proximity. The loop sequence contains a sequence that is complementary to the target nucleic acid. In the presence of the target, a duplex is formed between the molecular beacon and the target nucleic acid. When that occurs, the stem is broken, separating the fluorophore from the quencher. Consequently, the fluorophore is no longer quenched and fluorescence is restored." The paper continues by describing the adaptation of molecular beacons techniques to aptamers that specifically bind protein targets.

Following a short delay 23 during which the foregoing transfers in energy are occurring in the fluorophores, and continuing firing of the laser, the energized revised cloud is observed 25 to determine if any emissions are occurring at the emission frequency of the acceptor photoaptamer or the quencher photoaptamer, depending on the reporter system in use. That observation is accomplished with a spectrometer. If the Laser continues operation, some of the emitted light might be reflected back to the spectrometer. To avoid masking of the light frequency that is being sought, the spectrometer may include a filter to block out light of the wavelength being emitted by the laser, and pass the frequency of light anticipated from the FRET action only when the suspect bioagent is detected. The spectrometer may be equipped with appropriate decisional logic to determine if the light received is of the desired frequency 27 and above a threshold. If not the process ends, as represented at block 29. If so, the logic initiates an alarm 31 to warn personnel of the detection.

As one appreciates the foregoing embodiment of FIGS. 1 and 2 is improved in an embodiment that includes a preliminary reading of the ambient conditions prior to spraying the photoaptamer into the suspect cloud. Referring again to FIG. 1, such a preliminary reading is accomplished as the UAV 1 is flying toward cloud 3 during the initial pass. At that time the spectrometer 9 is aimed at the cloud 3 and the spectrometer readings are taken to determine the natural luminescence of the desired frequency of the photons radiated by the photoaptamer as light. Those emissions could result from the naturally occurring radiation or simply background radiation of that frequency. The intensity of that illumination is noted in the spectrograph and is used to establish a threshold level of the spectrograph (e.g. bias level) for the expected duration of the investigation. Then, at the stage of the process when the UAV reaches the farthest position, as represented on the right side of FIG. 1, and the spectrometer observation is made of the revised cloud 13, the spectrometer doesn't produce an indication unless the received light exceeds that threshold. Thereafter, the alternative embodiment functions the same as described for the first embodiment.

Any suitable spectrometer may be employed in the process, modified to include conventional wireless remote control module or circuitry. That could be one of the more expensive spectrometers such as the 0.3-meter spectrometers (McPherson Model 218). Alternatively less expensive spectrometers may be constructed along the designs referred to in U.S. Pat. No. 5,166,755 granted Nov. 24, 1992 to Gat or in U.S. Pat. No. 4,790,654 granted Dec. 13, 1988 to Clark, assigned to the present assignee.

Other embodiments of the invention may be presented in a more complex arrangement. As one probably noted the foregoing process checks to determine whether a suspect bioagent is present in the suspect cloud, and the testing is made for that bioagent. However, if that inspection proves negative, that could mean only that the speculation as to the identity of the bioagent was incorrect, and leaves open the possibility that some other deadly bioagent is present in the suspect cloud. One may then take another guess as to the nature of the bioagent, and repeat the foregoing process substituting different photoaptamers that are intended to link to a second-choice suspect bioagent. That procedure can be repeated until a particular bioagent is identified or until all possibilities have checked out negative.

As one appreciates, the foregoing tests are conducted in a serial order. Hence, a greater amount of time may be consumed to identify the bioagent or rule out all significant prospects, while the cloud continues drifting in the prevailing winds toward the intended target. A more complex embodiment that could speed up those tests would run the tests in parallel instead of in series. That is, tests for all possible suspect bioagents could be accomplished simultaneously. Such an embodiment requires that the photoaptamers for each of the bioagents in the library of suspect bioagents are included in the liquid that is sprayed as cloud 13 into suspect cloud 3. In such a complex embodiment, the laser of the first embodiment is replaced by a wireless, remote-controlled, tunable laser that can be programmed to sweep over a range of frequencies, automatically. Thus each of the various photoaptamers, which have different excitation frequencies, will receive appropriate energizing radiation at some point during the frequency sweep of the laser output. That sweep can be quite rapid, as example, over a frequency range of visible light at thirty cycles per second. The spectrometer would also monitor the complete range of emission frequencies and give a readout for each frequency of light that's received.

As is appreciated with such a mixture of aptamers, the amount of aptamer allocated to each antigen is less. Consequently, the greater the number of potential bioagents, the less the amount of photoaptamer allocated to any individual bioagent, and the lesser the intensity of the fluorescence that occurs in the presence of any individual bioagent in the cloud. Thus the greater the sensitivity of the spectrometer the better.

Reference was earlier made to the binding that occurs between the suspect bioagent and the photoaptamer. The mixing, actually, collision between the threat agent particles and the photoaptamers ("recognition particles") forms a second bulk aerosol cloud that resulted from binding between the two types of particles. An important phenomenon in the method is the mixing of threat agent particles and recognition droplets and the collision efficiency, E, between the two types of particles, threat agent and recognition droplets, where E can be defined as the ratio of the total number of collisions occurring between collector (recognition) particles and collecting (threat agent) particles to the total number of collecting particles in an area equal to the collector particle's effective cross-sectional area. A value of E=1 implies that all collecting particles in the geometric volume swept out by a moving collector particle will be collected, which is not the case. Usually that efficiency is less than 100% (i.e. E<1), although E can actually exceed unity if electrical effects are present. Similar considerations existed heretofore in the fields of cloud seeding and pollutant scavenging by precipitation and a wide body of literature is available on the collection efficiency in those fields, which applicant believes analogous. The mechanisms that should be accounted for whereby particles in the air reach the surface of a moving collector particle include Brownian diffusion, interception, and inertial impaction. It can be shown that the collision efficiency mainly depends on the size distribution, velocity, and viscosity of particles.

Collision efficiency between threat and recognition particles may be calculated by use of well-established algorithms (e.g. modified Stokes flow solutions, modified oseen flow solutions, and numerical solutions of the Navier-Stokes equations). These algorithms also allow the determination of the size distribution of recognition particles that leads to an optimal collection efficiency for threat agent particles. It is believed that the overall time from releasing of the liquid droplets to the bonding of the photo-aptamers is likely to occur in a period of a minute or so. Biochemical binding should be nearly completed within about 5 to 10 minutes in liquid phase. Liquid incubation time is likely to be limited by diffusion of the reagents, with aerosol kinetics being much faster.

As one appreciates, the methods presented in this specification, among other things, makes use of aptamers, photoaptamers and fluorophores that can attach to aptamers or photoaptamers to form a tagged aptamer or photoaptamer. The method does not invent either of the two substances, but, as next briefly described, notes how those substances are known to be obtained and offers some choices as candidates. It is expected that additional photoaptamers will be discovered by others for various kinds of biological proteins. The invention presents a way to use aptamers, old or new, in a new application or in a new way. Several photo-aptamers are available from the Somalogic company that are able to bind selectively to a given antigen. The TetraCore company also offers well characterized antibodies for simulants. Suitable photo-aptamer and/or antibody pairs are selected for a given target antigen and their efficiency tested. The Molecular Probes Company of Eugene, Oreg. also makes available fluorophore pairs of donors and acceptors.

The criteria for selecting a suitable fluorophore should include the absorption spectrum of the acceptor fluorophore overlapping the fluorescence emission spectrum of the donor fluorophore; the Forster radius of the donor/acceptor pair must be sufficiently long to yield rapid energy transfer; and, the lifetime for the donor should be substantially long compared to that of the donor for discrimination of the background emission by direct excitation.

Consider fluorophores. Pyrenebutyrate, which has a relatively long lifetime of ~100 ns, has been used as a donor in a time-resolved fluorescence resonance energy transfer for the immunoassay of human immunoglobulin protein (Morrison 1988). Unfortunately, pyrenebutyrate is relatively toxic and that is difficult to handle.

The rare earth ions are perhaps desirable candidates as donors, due to the relatively long lifetime illumination of several hundred μs to ms. In addition, those ions exhibit very high quantum yield and are relatively non-toxic. The fluorescence excitation band of europium fluorophores is relatively broad from ~300 to 370 nm, whereas the emission band is relatively narrow peaking at about 610 nm. A frequency-tripling-YAG laser at 355 nm can conveniently be used as an excitation source.

The series of Alexa Fluor and Cy fluorophores are suitable as acceptors. The lifetimes of those compounds are in general relatively short, only a few ns. Excitation spectra for those fluorophores overlap well with the emission spectrum of europium, in the range of 605 to 620 nm. In addition, the emission spectra of these acceptors are relatively distant from that of the europium to permit isolation from the donor emission by the use of an optical band filter.

In additional embodiments, multiple labeled photo-aptamers may be used to detect several biological agents through wavelength multiplexing of various acceptor emission bands, providing for the use of a common donor fluorophore. For example, the locations of the emission band of Alexa Fluor 647 and 680 appear of such sufficient difference that the emissions can each be isolated by use of different optical filters. The number of detectable agents increases further if similar multiplexing is used for the excitation wavelengths. It is believed that more than a dozen biological materials can be detected through such multiplexing methods.

The fluorophore 1-pyrenebutyrate is known as a short lifetime photon donor and B-phycoerythrin is known as a long lifetime acceptor dye. That pair has been used successfully by a third party in a time-resolved fluorescence resonance energy transfer (FRET) experiment. See Morrison, L. E. (1988), "Time-Resolved Detection of Energy Transfer: Theory and Application to Immunoassays," Analytical Biochemistry, 174:101-120.

"Nucleic acid ligands" include nucleic acids that are identified from a candidate mixture of nucleic acids, the nucleic acid ligand being a ligand of a given target, by the method comprising : a) contacting the candidate mixture with the target, wherein nucleic acids having an increased affinity to the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids. The foregoing is recognized as the methodology known as Systematic Evolution of Ligands by EXponential Enrichment or "SELEX" methodology, which is more precisely defined as follows: "SELEX" methodology involves the combination or selection of nucleic acid ligands, which interact with a target in a desirable manner, such as binding to a protein, with amplification of those selected nucleic acid. Optional iterative cycling of the selection and amplification steps allows selection of one (or a small number of) nucleic acids which interact most favorably with the target from a pool which contains a very large number of nucleic acids. Cycling of that selection and amplification procedure is continued until the desired goal of purity and selectivity in the nucleic acid ligand is achieved. The methodology is used to obtain nucleic acid ligands to proteins without first directly purifying the protein target. Amplification is a common term known to mean the making of additional copies as by the polymerase chain reaction process or "PCR."

"SELEX target" or "target" means any molecule of interest or compound of interest for which a ligand is desired. A target, as example, can be a protein, peptide, carbohydrate, glycoprotein, hormone, receptor, antigen, antibody, virus, substrate, metabolite, drug, bacteria, and the like. In this application, the SELEX targets include proteins, bacteria, viruses and small molecules.

As used herein, "nucleic acid ligand" is a non-naturally occurring nucleic acid having a desirable action on a target.

Nucleic acid ligands are often referred to as "aptamers." The term aptamer is used interchangeably with nucleic acid ligand in this application.

"Candidate mixture" is a mixture of nucleic acids of differing sequence from which to select a desired ligand. The source of a candidate mixture can be from naturally-occurring nucleic acids or fragments thereof, chemically synthesized nucleic acids or nucleic acids made by a comination of the foregoing techniques. In a preferred embodiment, the candidate mixture is varied and random.

"Nucleic acid" means either DNA, RNA, single stranded or double-stranded, and any chemical modifications thereof. Modifications include, but are not limited to, those which provide other chemical groups that incorporate additional charge, polarizability, hydrogen bonding, electrostatic interaction, crosslinking, and functionality to the nucleic acid ligand bases or to the nucleic acid ligand as a whole.

It is known that any protein molecule can be fashioned into an aerosol particle. Hence, any free protein can be used as a surrogate for a real biological agent. The protein Thrombin is one such surrogate protein and an anti-Thrombin aptamer, with the "best" one called G15D5dMB. The use of G15D5dMB in an aerosol is essentially identical to that in a liquid because the liquid is the same, it's just broken up into smaller droplets, each of which acts as a test tube. The small size of that simulated test tube makes the mixing of the ingredients occur more quickly and the reaction happen more rapidly. Two fluorophores of the donor/quencher variety useful for tagging molecules are named fluorescein/DABCYL, respectively. Those fluorophores can be used to tag any photoaptamer. As skilled microbiologists are aware, there are antibodies to each and every toxin, toxic protein. Because of that the microbiologists also recognize that one can create an aptamer or photoaptamer for each of those toxic proteins. One need only carry out the known SELEX procedure earlier herein described. An interesting background to SELEX is presented in U.S. Pat. No. 6,730,482 granted May 4, 2004 to Gold et al, assigned to SomaLogic, Inc.

It is believed that the foregoing description of the preferred embodiments of the invention is sufficient in detail to enable one skilled in the art to make and use the invention without undue experimentation. However, it is expressly understood that the detail of the elements comprising the embodiment presented for the foregoing purpose is not intended to limit the scope of the invention in any way, in as much as equivalents to those elements and other modifications thereof, all of which come within the scope of the invention, will become apparent to those skilled in the art upon reading this specification. Thus, the invention is to be broadly construed within the full scope of the appended claims.

What is claimed is:

1. A method for detecting the presence of airborne molecules of a target substance comprising the steps of:

producing an aerosol of ligands to the target substance in a region of sky believed to contain airborne molecules of said target substance to produce in said region at least some airborne molecules of said target substance bound respectively to said ligand to define a revised aerosol in said region of sky, if airborne molecules of said target substance were present in said region;

said ligands having the collective property of accepting light of a first frequency and emitting light of a second frequency displaced from said first frequency;

directing light of said first frequency into said revised aerosol, wherein at least some of said light is incident on at least some of said ligands; and inspecting said revised aerosol for emissions of light of said second frequency following said step of directing light; and initiating a perceptible warning if light of said second frequency is observed during said step of inspecting; and wherein said step of producing an aerosol of ligands includes any of the steps of spraying, releasing or depositing ligands in a liquid base and wherein said liquid base comprises ethylene glycol.

2. The method for detecting the presence of airborne molecules of a target substance as defined in claim 1, wherein said ligands comprise a plurality of pairs of complementary photoaptamers, each pair of which is capable of binding to a respective molecule of said target substance, whereby said complementary photoaptamers in a pair are held by said molecule in close enough proximity, wherein one photoaptamer in each said pair of complementary photoaptamers is bound to a donor fluorophore to form a first fluorophore-photoaptamer conjugate, wherein said first fluorophore-photoaptamer conjugate releases energy without emitting a photon in response to being exposed to light-of said first frequency, and the other photoaptamer of said pair is bound to an acceptor fluorophore to form a second fluorophore-photoaptamer conjugate responsive to receiving energy released from said first fluorophore for emitting light of said second frequency.

3. The method for detecting the presence of airborne molecules of a target substance as defined in claim 1, wherein said ligand comprises a photoaptamer that includes two conjugate fluorophores, one of said conjugate fluorophores being a donor fluorophore for emitting light of a second frequency when exposed to light of said first frequency and the other of said conjugate fluorophores being a quencher fluorophore for quenching emission of light of said second frequency from said one fluorophore when said second fluorophore is in close proximity to said first fluorophore.

4. The method for detecting the presence of airborne molecules of a target substance as defined in claim 1, wherein said step of initiating a perceptible warning if light of said second frequency is observed during said step of inspecting comprises the step of initiating an audible alarm if light of said second frequency is detected.

5. A method for detecting the presence of airborne molecules of a target substance comprising the steps of:

producing an aerosol or pairs of fluorescent dye-photoaptamer conjugates to said target substance in a region of sky believed to contain airborne molecules of said target substance to produce at least some airborne molecules of said target substance bound respectively to said fluorescent dye-photoaptamer conjugates in said region, if airborne molecules of said target substance are present in said region;

wherein in the case of said photoaptamer, one fluorescent dye molecule in said pair of fluorescent dye-photoaptamer conjugates being a donor fluorophore and the other dye molecule of said pair being a quencher fluorophore;

directing light into said aerosol, wherein at least some of said donor fluorophores receives and absorbs some of said light, said light being of a frequency that is accepted and absorbed by said donor fluorophore; and monitoring said aerosol for emissions of light of a frequency characteristic of the absence of quenching caused by photoaptamer binding to its target; and issuing an alarm on detection of said emissions;

said step of producing said aerosol includes any of the steps of spraying, releasing or depositing fluorescent dye-photoaptamer conjugates in a liquid base and wherein said liquid base comprises ethylene glycol.

6. The method as defined in claim 5, wherein said step of directing light into said aerosol comprises the steps of pointing the output of a laser into said aerosol and powering said laser.

7. The method for detecting the presence of airborne molecules of a target substance as defined in claim 5, which includes, prior to the step of producing an aerosol, the steps of viewing said target substance for emissions of light of a frequency characteristic of the absence of quenching caused by said photoaptamer binding to its target to establish a base level of background emissions.

* * * * *